(12) United States Patent
Kocher et al.

(10) Patent No.: US 11,430,553 B1
(45) Date of Patent: Aug. 30, 2022

(54) GREEN SCREEN—HEALTH VERIFICATION SYSTEM (GS-HVS)

(71) Applicants: Robert William Kocher, McLean, VA (US); Douglas Earl Dyer, Herndon, VA (US); John Shelly Bowling, II, Reston, VA (US)

(72) Inventors: Robert William Kocher, McLean, VA (US); Douglas Earl Dyer, Herndon, VA (US); John Shelly Bowling, II, Reston, VA (US)

( * ) Notice: Subject to any disclaimer, the term of this patent is extended or adjusted under 35 U.S.C. 154(b) by 0 days.

(21) Appl. No.: 17/128,715

(22) Filed: Dec. 21, 2020

(51) Int. Cl.
| | |
|---|---|
| *G16H 15/00* | (2018.01) |
| *G06K 19/06* | (2006.01) |
| *G06K 7/10* | (2006.01) |
| *G06K 7/14* | (2006.01) |
| *G07C 9/00* | (2020.01) |
| *G16H 50/30* | (2018.01) |
| *G16H 50/00* | (2018.01) |
| *G16H 40/67* | (2018.01) |
| *G16H 50/20* | (2018.01) |
| *G16H 70/20* | (2018.01) |
| *G06Q 10/10* | (2012.01) |
| *G16H 40/20* | (2018.01) |
| *A61B 5/00* | (2006.01) |
| *G16H 10/65* | (2018.01) |
| *G16H 10/60* | (2018.01) |
| *G06Q 50/26* | (2012.01) |

(52) U.S. Cl.
CPC ............ *G16H 15/00* (2018.01); *A61B 5/7465* (2013.01); *G06K 7/1095* (2013.01); *G06K 7/1447* (2013.01); *G06K 19/06112* (2013.01); *G06Q 10/105* (2013.01); *G07C 9/00* (2013.01); *G16H 10/60* (2018.01); *G16H 10/65* (2018.01); *G16H 40/20* (2018.01); *G16H 40/67* (2018.01); *G16H 50/00* (2018.01); *G16H 50/20* (2018.01); *G16H 50/30* (2018.01); *G16H 70/20* (2018.01); *G06K 7/1417* (2013.01); *G06K 19/06037* (2013.01); *G06Q 50/265* (2013.01)

(58) Field of Classification Search
None
See application file for complete search history.

(56) References Cited

U.S. PATENT DOCUMENTS

2020/0279464 A1* 9/2020 Llewelyn ............... G16H 15/00

\* cited by examiner

*Primary Examiner* — Kristy A Haupt

(57) ABSTRACT

A system and method of testing, recording, tracking, and verifying the health of an individual to other persons while providing confidence that the individual user has taken and reported to at least one medical measurement, and this measurement has been identified as normal or not normal to the specific individual user, is provided. A medical instrument which is self-administered by the said individual user and a Green Screen Health Verification System (GS-HVS) server are provided. Software that contains prearranged decisions and protocols to provide guidance to said individual user and to an individual user's supervisor and records any abnormal reporting from said individual user and provides alerts based on said protocol. Software returns guidance from said GS-HVS server to said individual user, and upon said GS-HVS indicting that said individual user has good health, software displays a good health status or "Green Screen" on said individual user's said mobile device.

20 Claims, 3 Drawing Sheets

GREEN SCREEN—HEALTH VERIFICATION SYSTEM (GS-HVS)

CROSS-REFERENCE TO RELATED APPLICATIONS

None

FEDERALLY SPONSORED RESEARCH

None

BACKGROUND

Field of the Invention

The invention relates to the general field of an anonymous individual health verification, without obtaining the identity of the individual. Specifically, the invention relates to a system and method for allowing a plurality of individuals to gather together for an event, such as a music concert, in a closed venue, after determining that all of the individuals permitted to enter the venue are healthy and do not appear to have the 2019 novel coronavirus disease (COVID-19) or other similar diseases, without putting healthy individuals at risk. The Green Screen system and method of the invention verifies that infected individuals are not permitted to enter the venue, in order to keep the non-infected individuals safe. The Green Screen system and method only requires verification of health at the venue boundary, by requiring a third party to verify the health of individuals seeking entry to the venue.

Description of the Related Art

In the related art, the technology for verification includes the use of a block chain to share and verify anonymous information. However, a block chain has drawbacks is it is more complicated and consumes far more communication and processing resources than the claimed system and method, which uses a centralized server, mobile devices, and a process which enables health status verification without sacrificing anonymity or requiring any other information from each individual user. Thus, it is important to be able to overcome the drawbacks associated with using blockchain to share and verify anonymous information, and in particular to be able to use a far less complicated operating system, which consumes far more communication and processing resources. To overcome the problems associated with the related art, it is beneficial to use a system and method which uses a centralized server, mobile devices and a new and unobvious process which enables health status verification without sacrificing anonymity or requiring any other information from the individual user seeking entry to the venue.

SUMMARY OF THE EXEMPLARY EMBODIMENTS OF THE INVENTION

The present invention is directed to a system and method enabling an individual to share health status anonymously with a third party in such a way as to enable the third party to verify the information by checking the individual's health status with another, trustworthy source, namely a server, running software specified by and on behalf of the individual's group. The individual's group sets the criteria for assessing health status, and a systems administrator, in direct control of the server, and working on behalf of the group, ensures that the server is making health assessments according to these criteria. As a result, the third party has a reason to trust the server's response when checking an individual's health status. Furthermore, the invention includes the ability of an individual's supervisor or an authorized medical provider to amend the system's assessment of the individual's health status to account for special conditions, which are unknown to the server.

A systems administrator establishes a group on the server for collecting health measurements for a set of individuals associated with the group; a leader of the group establishes thresholds for the measurements to define a status of 'compliant' or 'not compliant with protocol' based on an individual's actual measurement; the leader updates the server software with these thresholds for the group either directly or with the assistance of the systems administrator.

A third party, with the intent to be able to verify health status information, enrolls with the server to establish an account by choosing a unique account name and password. The third party has access to the groups and their associated thresholds for health measurements defining a status of 'compliant' or 'not compliant with protocol'. Two protocols are used in determining the health status and access allowability of an individual user. The first protocol is referred to as the computer protocol. This computer protocol consists of a set of predetermined rules for the computer to respond, based on the individual user's input. The second protocol is referred to as the advice protocol, whereby a supervisor or medical advisor provides advice to the individual user.

Before sharing, an individual enrolls with the server to establish an account associated with the individual's group by choosing a unique account name and password; the server does not know the identity of the individual, and no other person can know the identity of the individual if the account name does not indicate it, but the server does associate the new account with the individual's group.

Before sharing, the individual uses a health device to measure an aspect of the individual's health and, with the established account, uploads this measurement to the server. The server stores the measurement for the individual and based on the thresholds selected by the group leader and set in the server's software, the server assesses the measurement and replies with the health status of 'compliant' or 'non-healthy.' It is this health status that the individual intends to share, and in an exemplary embodiment, the health status is displayed on the individual's mobile device in an app, as a 'Green Screen' if the health status of the individual is 'compliant' or a 'Yellow Screen' if the health status of the individual is 'non-healthy.'

Normally, the individual chooses to only share their health status with a third party, and does not share other information, such as the individual's identity. However, it is important that a third party or any system with whom the information is shared must be able to verify the accuracy of the individual's shared health status. To achieve this efficiently, an embodiment of the Applicant's invention comprises a mobile device app, and server. Additional embodiments include a kiosk or access system. The individual can share their current health status stored on the server by requesting, receiving and displaying a server-generated image in their app interface that indicates their health status and enables verification. In an exemplary embodiment, the image displayed is a 'Green Screen' if the individual is determined to be healthy or a 'Yellow Screen' is displayed if the individual is determined to be 'non-healthy,' and in either case, the displayed image includes a server-generated image, such as a Quick Response (QR) barcode.

An exemplary embodiment provides for a system testing, recording, tracking, and verifying the health of an individual user to other persons while providing confidence that the individual user has taken and reported a least one medical measurement, and this measurement has been determined to be normal or not normal to the specific individual user. The system of the exemplary embodiment provides a medical instrument designed to be self-administered by the said user or assisted by another person; a portable communication device such as a cell phone, laptop, electronic tablet with a digital display and capable of two-way communications with digital communication systems; a communications system that links said portable communications device with server systems; a server system referred to as the Green Screen Health Verification System (GS-HVS) server which includes software that communicates with said user's portable communication device. Software that contains prearranged decisions and protocols to provide guidance to said individual user and to said user's supervisor or medical advisor as to what action said individual user should do; software that records all medical reports from said individual user; software that recognizes any abnormal reporting from said user and provides any alerts based on said protocol or protocols. A supervisor or medical advisor can provide advice to said individual user on any possible problems with said individual user based on said individual user's input to said GS-HVS; software that returns guidance from said GS-HVS server to said individual user if they are medically accept able to go to work or should take other actions such as contacting said supervisor for additional direction. In the case where said GS-HVS indicted that said individual user has good health, software that communicates with said individual user's said mobile device and displays a good health status or "Green Screen" on said User's said mobile device; and, software that allows said individual user to present said GS-HVS results as a screen view to a third party that said individual user desired to show the results to confirm health status.

According to an exemplary embodiment, a method of testing, recording, tracking, and verifying the health of an individual user to other persons while providing confidence that the individual user has taken and reported to at least one medical measurement, and this measurement has been identified as normal or not normal to the specific individual user, is provided. The method including the steps of: providing a medical instrument which is self-administered by the said individual user or assisted by another person; providing a portable communication device with a display and two-way communications with digital communication systems; providing a communications system that links said portable communications device with server systems; providing a Green Screen Health Verification System (GS-HVS) server which includes software that communicates with said individual user's portable communication device; providing software that contains prearranged decisions and protocols to provide guidance to said individual user and to said individual user's supervisor or medical personal as to what action said individual user should do; providing software that records all medical reports from said individual user; providing software that recognizes any abnormal reporting from said individual user and provides 'yellow screen' alerts based on said protocol; providing a supervisor or medical advisor that provides advice to said individual user on any possible problems with said individual user, based on said individual user's input to said GS-HVS; providing software that returns guidance from said GS-HVS server to said individual user in response to the individual user being medically acceptable to go to work or take other action including contacting said supervisor for additional direction when the individual is not medically able to go to work; and wherein upon said GS-HVS indicting that said individual user has good health, software displays a good health status or 'Green Screen' on said individual user's said mobile device.

REFERENCE NUMERALS RELIED UPON IN THE APPLICATION

Element 100 represents a flowchart of system operation where an individual user enters temperature for processing and determination of whether they are healthy or unhealthy.

Element 105 represents an individual user taking their temperature.

Element 110 represents an individual user entering their temperature into the GS-HVS system.

Element 115 represents a computer decision protocol.

Element 120 represents a yellow screen.

Element 125 represents the individual user with a yellow screen notifying a supervisor.

Element 130 represents a green screen.

Element 135 represents authorization for green screen access.

Element 140 represents a decision by a supervisor.

Element 145 represents a supervisor not overriding a yellow screen and providing other guidance.

Element 150 represents date/time validation of a green screen.

Element 155 represents use for visual verification.

Element 160 represents use for access or verification.

Element 165 represents GS-HVS verification communications.

Figure 3:
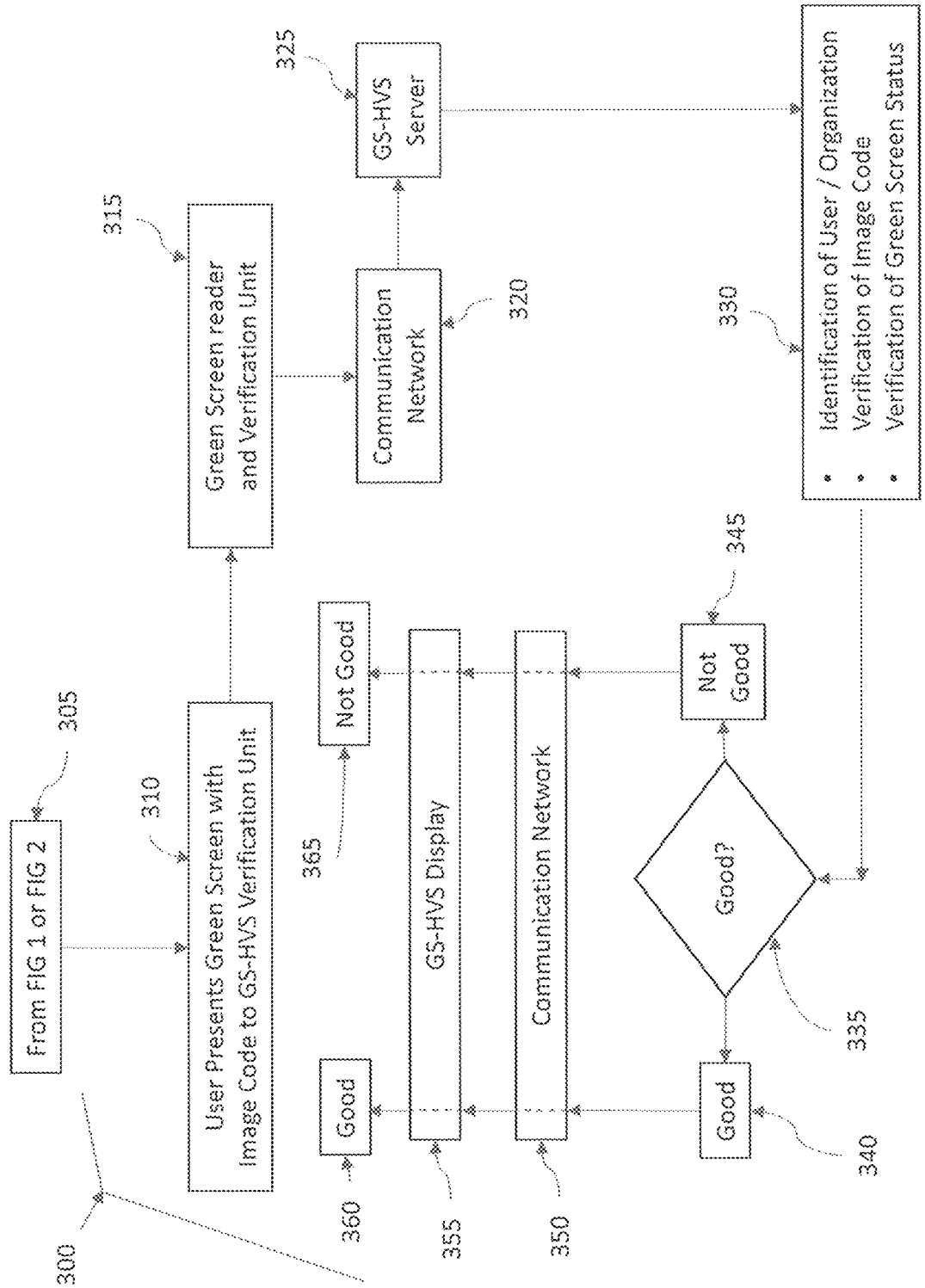
FIG. 3 is directed to a flowchart where an individual user receives their health determination and presents their health determination for entry or discussion with medical personnel.

Element 170 represents continuation on FIG. 3.

Element 200 represents a flowchart of system operation where an individual user is taking and entering medical measurements for processing and determination of whether they are healthy or unhealthy.

Element 205 represents an individual user taking medical measurements.

Element 210 representing an individual user entering their medical measurements into the GS-HVS system.

Element 300 represents an individual user presenting a health determination image code to the GS-HVS verification unit and verification.

Figure 1:
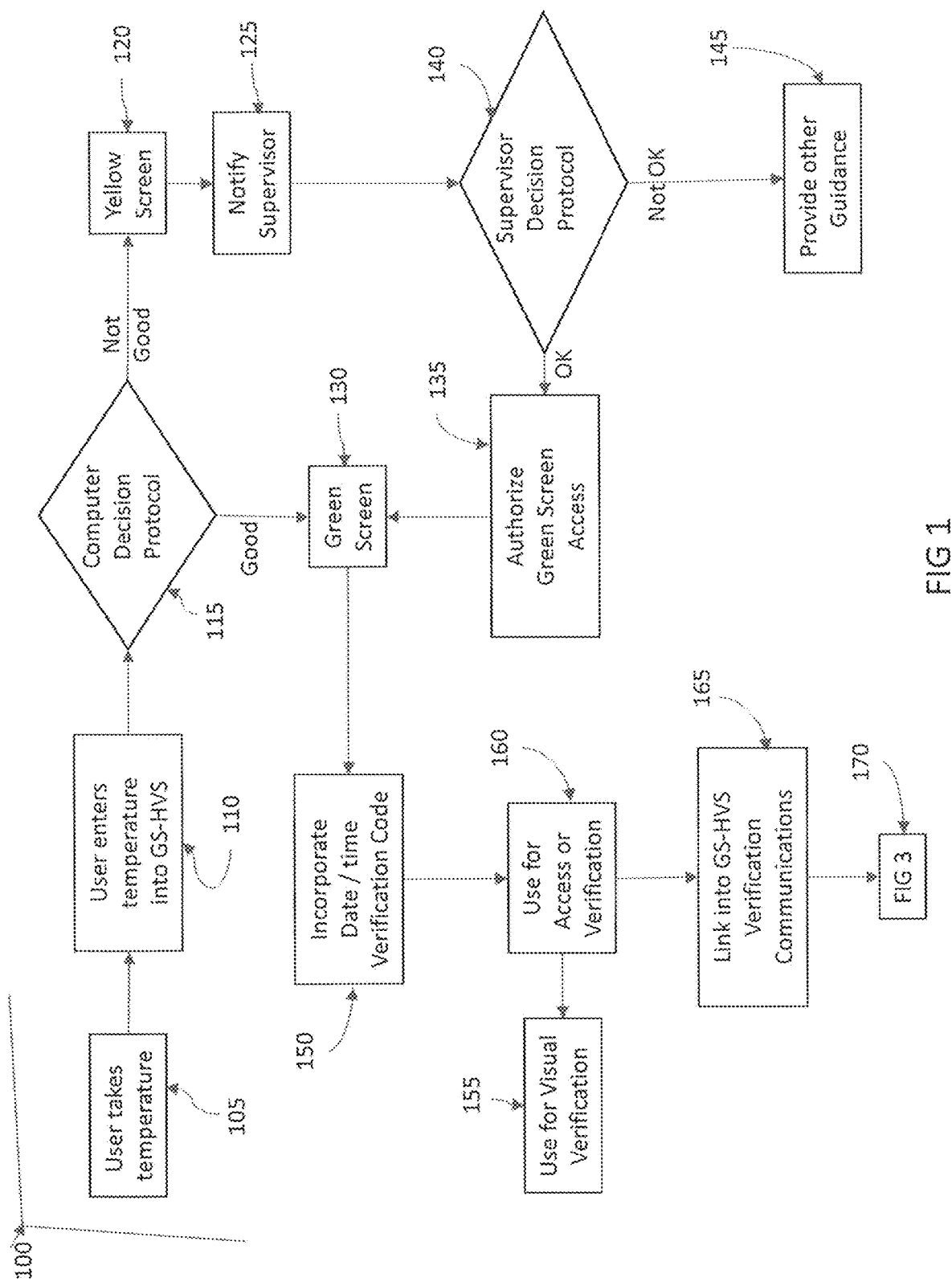
FIG. 1 is directed to a flowchart of system operation where an individual user enters temperature for processing and a determination of whether they are healthy or unhealthy.
Figure 2:
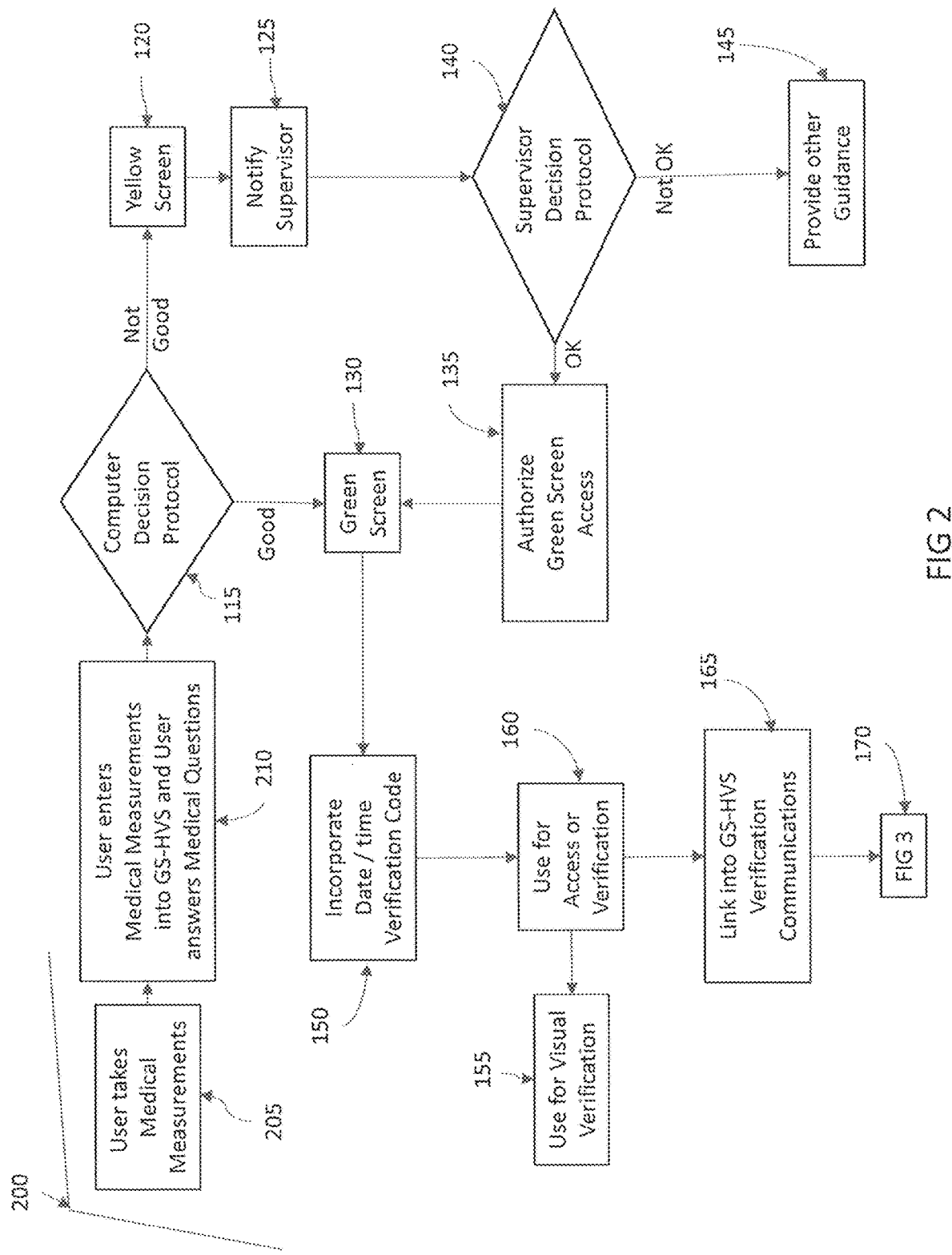
FIG. 2 is directed to a flowchart of a situation where an individual user enters medical measurements for processing and a determination of whether they are healthy or unhealthy.

Element 305 represents continuation from FIG. 1 or 2.

Element 310 represents an individual user presenting their Green Screen image code to the GS-HVS verification unit.

Element 315 represents a green screen reader and verification unit.

Element 320 represents a communication network.

Element 325 represents the GS-HVS server.

Element 330 represents identification of the individual user, verification of the user and the image code and verification of green screen status.

Element 335 represents a query as to whether the individual user status compliant with protocol i.e. 'good' or not compliant with protocol i.e., 'not good.'

Element 340 represents that the individual is compliant with protocol ('good').

Element 345 represents that the individual user is not compliant with protocol ('not good').

Element 350 represents a communications network.

Element 355 represents the GS-HVS display.

Element 360 represents the system GS-HVS returning a 'good health' status in compliance with protocol.

Element 365 represents the GS-HVS rejecting compliance with protocol.

DETAILED DESCRIPTION OF EXEMPLARY EMBODIMENTS OF THE INVENTION

Using an app on the individual user's mobile device, the individual user requests their verifiable health status, and the server generates a web page including the health status (such as 'Green Screen' or 'Yellow Screen') and a QR code and sends it to the individual user's app in response, where the app displays the information on the individual user's mobile device.

The QR code includes the server's URL as well as a unique verification code, associated with the individual user; that the server generates and can subsequently use to retrieve the individual user's current status. In addition, in an exemplary embodiment, the server saves an expiration time for the verification code. This means that after a set amount of time, the ability of an individual user to enter the venue ends.

To verify the individual's health status, a third party can scan the individual user's QR code, displayed in the individual user's app on the individual user's mobile device, with the third party's own camera-equipped device, a process that, with the appropriate software on the third party's device, automatically requests the individual user's current status from the server. The verification code included in the individual user's QR code is sent to the server as part of the request for the individual user's current status, and the third party's account name is also sent as part of the request.

In response to the request for the individual user's current status, the server checks to see whether the third party's account name exists, and if so, in response to an individual user existing that corresponds with the verification code, if the request has been made before the expiration time associated with the verification code, the server looks up the individual user's current health status and group and returns that information in a health status message that can be interpreted by either a human or a machine. Otherwise, the server responds with a problem message, interpretable by a human or machine, explaining the problem.

Optionally, in an exemplary embodiment, the server also checks to see how many times it has provided the individual user's current status using the verification code, and will not provide the individual user's status if the current request exceeds some threshold (such as 1 time) to the same third-party access system. This is to prevent multiple individuals from entering the same venue using another individual's green screen. Note that the third party could be a human or it could be a machine, such as a kiosk or a controller for access control equipment; such as a turnstile, electronic lock, or automatic door. If the third party is a human, then the health status message or error message returned by the server is displayed in the third party's device and can be read by the third party to verify the individual user's health status and access to the venue.

Alternatively, if the third party is a machine, then the health status message or error message returned by the server is interpreted in software, and the machine uses software to perform an appropriate action, such as sending a control signal to an electronic lock so as to permit the individual entry via access control equipment, such as an electronically locked door, automated turnstile, colored light or electronic gate, if the individual's health status is verified 'healthy;' or displaying information for the individual in response to the individual's health status being verified 'not compliant with protocol' or the server has sent an error message, in which case access is not permitted.

An exemplary embodiment includes the ability of the individual to also upload additional health information that can be verified to a third-party anonymously linking to the image code along with supporting evidence for sharing with the system. This allows the GS-HVS to verify to a third-party additional health information. For example: sharing the fact that you've had a COVID vaccination along with a photo of the vaccination record.

Illustrated in FIG. 1 is a flowchart relating to of system operation where an individual user enters temperature for processing and determination of whether they are healthy or unhealthy. If determined to be healthy, a green screen is provided on their smart phone or tablet, etc. In the green screen is a verification image code or QR code. The verified green screen then permits the individual user to enter the venue. Element 105 represents a user taking their temperature. The individual user then enters their temperature into the GS-HVS system as illustrated at element 110. As illustrated in element 115, a system computer, using protocols, makes a decision as to whether the individual user has a temperature that is healthy. In response to the individual user having a temperature that is considered to be not good, i.e., unhealthy, a yellow screen appears on the individual user's smart phone, tablet, etc. as illustrated at element 120. With the yellow screen, the individual user cannot enter the venue. The individual user will then notify a supervisor to ask for assistance, as illustrated by element 125. The supervisor or medical professional will then consider other information that the individual provides, such as proof of a recent COVID-19 test showing that he/she does not have COVID-19. The supervisor, as illustrated in element 140, may make a decision to override the yellow screen and give the individual use a green screen to allow entry into the venue. Alternatively, the supervisor may decide not to overcome the yellow screen and may provide other guidance to the individual user who is trying to enter the venue, as illustrated in element 145. The other guidance may be for the individual user to seek medical attention.

If the supervisor overrides the yellow screen, the supervisor with authorize green screen access as illustrated in element 130. The authorized green screen will incorporate the date/time of the green screen decision, as well as a validation code, which may be an image code or a QR code, as illustrated in element 150. The individual user may then use the verified green screen for access or verification as illustrated in element 160 or by using visual verification, as illustrated in element 155. As illustrated in element 165, the validation and verification of the image code or QR code is linked to the GS-HVS verification communications device.

Turning to FIG. 2, element 200 represents a flowchart of system operation where an individual user is taking and entering medical measurements for processing and determination of whether they are healthy or unhealthy enough to enter the venue. FIG. 2 is similar to FIG. 1. The difference being the two figures is that in FIG. 1, the individual user's temperature is taken, whereas in FIG. 2 that individual user takes medical measurements, such as pulse and blood pressure, etc. It will be understood by those of ordinary skill in the art that the medical tests are not limited to pulse and blood pressure and that numerous other medical tests, may readily be used. In element 205, the individual user takes medical measurements. In element 210 the user enters the medical measurements into the GS-HVS and the user additionally answers medical questions posed to the user. At the end of both of the flowcharts in FIGS. 1 and 2, the flowcharts conclude with the individual user proceeding to FIG. 3, as in element 305.

As illustrated in element 300, the flowchart represents an individual user presenting a health determination screen with an image code or QR code for entry into the venue. The health determination screen is presented to the GS-HVS verification unit along with the image code or QR code, as illustrated in element 310. Illustrated in element 315 is a green screen reader and verification unit. The verification unit communicates with the GS-HVS server 325 via communications network 320. The GS-HVS server outputs to element 330 which identifies the individual user, verifies the image code or QR code and verifies the green screen status. After the identification and verification steps, a determination is made at element 335 as to whether the health of the individual user is 'compliant' or 'not good.' If 'good,' at 340 the green screen is correct, and if 'not good' at 345 a yellow screen is presented. Each of these outcomes are outputted, via communications network 350 to the GS-HVS display 355. A 'compliant' outcome is illustrated at 360 as a verification of the green screen, signal light, or other access indication. A 'not good' outcome 365, is displayed as a yellow screen, colored light or a screen stating that there is a problem, which prohibits entry by the individual user.

An example of use of the Green Screen system for an event venue such as a music concert is as follows. Certain events, such as a live music concert, involve the gathering together of multiple individuals in close proximity at an enclosed venue. If there is no way to verify that all individuals entering the venue are healthy, then an infected individual inside the venue of the event might infect others inside the venue, putting healthy individuals at risk. In contrast, using the Green Screen system provides a way to verify all individuals gathering in close proximity are healthy, then healthy individuals are not at risk of becoming infected inside the venue because any infected individual attempting to enter the venue would be prevented from doing so. With the Green Screen system and method, the venue only requires verification at the venue boundary. In the operation described above, the venue requires a 'third party' to verify individuals wishing to enter.

The third party being used as a verification method for people wishing to enter a controlled area may optionally also impose minimum standards for those requesting access to the area. In this context, an individual may be rejected by the third-party verifier even if the individual has a passing health status from the GS-HVS. For example, if the user passes their group's computer decision protocol, but their group's computer decision protocol does not meet the standard of the third party's venue, the individual's passing health status may be rejected. In this process, the third party uses the GS-HVS to scan the QR code from the individual seeking access. Next, the GS-HVS server then determines if the individual has a passing health status. Then, the GS-HVS server determines if the individual's group's computer decision protocol meets the minimum standard of the venue. Finally, the GS-HVS server returns a result to the third party which determines if the individual seeking access is permitted entry. A third party may optionally configure a wide variety of minimum standards including but not limited to checking for symptoms, a specific temperature check, or evidence for vaccination. If an individual's group does not check for at least the minimum standards that the third party is expecting, the results of its computer decision protocol will be rejected.

Another way to verify individuals entering venue is to have a human as the third party. In this case, the human could use a communications-enabled mobile device such as a smart phone or Wi-Fi-connected tablet to scan the QR code from the app on the mobile device of each individual wishing to enter the venue. Alternatively, the third party's device might be a fixed computer with a camera and appropriate software. Regardless of the third party device, scanning the QR code would initiate a request with the server to send the individual's health status, and the received health status could be displayed on the third party's device, enabling the human to permit entry to every 'compliant' individual and deny entry to any 'not compliant with protocol' individual or in the case of an error message.

Another, more automated way is to use automated access control equipment at the venue boundary, in which case the venue's third party is a controller, a computer (machine). The controller would obtain a scan of an individual's Green Screen display, reading the QR code to automatically request and receive the individual's health status from the server. The controller would, using automatic access control equipment such as an electronic door lock, security turnstile, automatic gate, or colored light, permit or deny entry to the individual just as in the previous paragraph.

Another alternative is to use a kiosk near the entry of the venue that operates in a similar way but provides a token, such as a wrist band, if the individual is verified as 'compliant'.

Optionally, the kiosk could also receive the ticket for the event. After receiving the ticket, the individual could enter the venue by showing the token to a security guard.

The following definition of terms provide a specific definition for terms used in the application.

Computer Decision Protocol—can be simple static guidance i.e.; if the temperature is above 100.4, then respond with yellow screen. Protocol can be complex or dynamic such as comparing the temperature to a channel orange based on time. The decision protocol can also take into consideration the medical measurements and the answer to the medical questions.

Supervisor Decision Protocol—can be simple static i.e., if the user's temperature is above 100.4, instruct the user to quarantine and request a test or see a doctor. Or, if the User's temperature is 0.2 F above their Warning Temperature, have the users stay home and take their temperature every 30 minutes to see if it's going down. Then consult with medical personnel.

Computer and Supervisor Decision Protocols are established by each organization for their own personnel. The protocol would take into consideration medical risk, which can be by individual, if an individual has a particular medical profile, privacy, processing of personnel that report a problem.

Medical Instrument: any instrument that measures the biological function and status of a human body and be administered by the user or assisted by other person. For example, thermometer, pulse measuring device, blood pressure device, etc.

Image Code: includes bar codes, two-dimensional codes, PKI codes, secret codes, image codes, QR, etc.

Although different exemplary embodiments have been shown and described, the invention is not limited to the exemplary embodiments because other exemplary embodiments would be readily understood by those of ordinary skill in the art. The invention is defined by the scope of the appended claims.

What is claimed is:

1. A Green Screen Health Verification System (GS-HVS) for testing, recording, tracking, and verifying the health of an individual user to other persons while providing confidence that the individual user has taken and reported at least one medical measurement, and this measurement has been determined to be normal or not normal to the specific individual user, the system comprising:
   information from a medical instrument designed to be self-administered by the said individual user or assisted by another person;
   a portable communication device comprising one of a cell phone, laptop or electronic tablet with a digital display and two-way communications with digital communication systems;
   a communications system that links said portable communications device with a GS-HVS server;
   said GS-HVS server includes software that communicates with said individual user's portable communication device;
   software that contains prearranged decisions and protocols to provide guidance to said individual user and to said individual user's supervisor or medical advisor as to what action said individual user should take;
   software that returns guidance from said GS-HVS server to said individual user stating when they are medically acceptable to go to work or should take other actions such as contacting said supervisor for additional direction;
   where said GS-HVS indicated that said individual user has good health, software that communicates with said individual user's said mobile device and displays a good health status or "Green Screen" on said individual user's said mobile device;
   software that allows said individual user to present said GS-HVS results as a screen view to a third party that said individual user desired to show the results to confirm health status;
   software that records all medical reports from said individual user; software that recognizes in accordance with computer protocol any abnormal reporting on a health question list from said individual user and provides any alerts based on said computer protocol; and,
   a supervisor or medical advisor that provides advice in accordance with an advice protocol to said individual user on any possible problems with said individual user based on said individual user's input to said GS-HVS.

2. The system of claim 1, wherein software allows the individual user's supervisor or medical advisor to change the said individual user's status to a Green Screen or good health status.

3. The system of claim 1, wherein the GS-HVS server embeds in the Green Screen a verification image code to confirm the authenticity of said Green Screen.

4. The system of claim 3, wherein the embedded image code contains a time stamp wherein the Green Screen validity expires after a specified amount of time.

5. The system of claim 4, wherein the embedded image code contains additional medical information such as but not limited to the history of the individual, if the individual user had received the COVID vaccine, if said individual user has had the COVID virus, dates of said vaccines, infections, or other infectious disease data.

6. The system of claim 1, wherein the individual user presents the Green Screen with an image code on with said individual user's mobile device to an access system comprising:
   an electronic image code reader,
   a communication system that links said image code reader to a GS-HVS server;
   software on said GS-HVS server that verifies said image code identification, authorization, and said Green Screen status; and,
   software on said GS-HVS that responds through said communication system that said image code reader by sending a signal indicating said individual user is good for access or not good for access.

7. The system of claim 1, wherein the portable communication device is a cell phone, laptop, or electronic tablet.

8. The system of claim 1, wherein the portable communication device has a digital display.

9. The system of claim 1, wherein the software that displays the "good Health" status communicates with said individual user's said mobile device.

10. The system of claim 1, wherein the software that allows said individual user to present said GS-HVS results as a screen view to a third party that said individual user desires to show the results to in order to confirm health status.

11. The system of claim 1, wherein the GS-HVS server embeds in the Green Screen a verification image code to confirm the authenticity of said Green Screen.

12. The system of claim 11, further comprising the embedded image code contains a time stamp wherein the Green Screen validity expires after a specified amount of time.

13. A method for testing, recording, tracking, and verifying the health of an individual user to others persons while providing confidence that the individual user has taken and reported a least one medical measurement, and this measurement has been determined to be normal or not normal to the specific individual user, the system comprising:
   providing a medical reading from a self-administered medical device by said individual user or assisted by another person;
   communicating said medical reading through a portable communication device to a Green Screen Health Verification System (GS-HVS) server;
   comparing said medical reading to a computer decision protocol on said GS-HVS server;
   transmitting in accordance with said computer decision protocol the results of said computer decision protocol back to said individual user;
   transmitting in accordance with said computer decision protocol the results of said computer decision protocol to said individual user's supervisor or medical advisor;
   comparing said medical reading to an advice protocol; and, communicating in accordance with said advice protocol between said individual user and said supervisor or medical advisor to obtain more information from said individual and concluding with a recommendation of action for said individual or authorization for access.

14. The method of claim 13, embedding a verification image code in the Green Screen to confirm the authenticity of said Green Screen.

15. The method of claim 14, embedding an image code that contains a time stamp wherein the Green Screen validity expires after a specified amount of time.

16. The method of claim 15, embedding additional information into the image code that contains additional medical information such as but not limited to, whether the individual user had received the COVID vaccine, whether said individual user has had the COVID virus, dates of said vaccines, infection, or other infectious disease data.

17. A method of testing, recording, tracking, and verifying the health of an individual user to other persons while providing confidence that the individual user has taken and reported to at least one medical measurement, and this measurement has been identified as normal or not normal to the specific individual user, the method comprising the steps of:
- providing a medical instrument which is self-administered by the said individual user or assisted by another person;
- providing a portable communication device with a display and two-way communications with digital communication systems;
- providing a communications system that links said portable communications device with server systems;
- providing a Green Screen Health Verification System (GS-HVS) server which includes software that communicates with said individual user's portable communication device;
- providing software that contains prearranged decisions and protocols to provide guidance to said individual user and to said individual user's supervisor or medical advisor as to what action said individual user should do;
- providing software that records all medical reports from said individual user;
- providing software that returns guidance from said GS-HVS server to said individual user in response to the individual user being medically acceptable to go to work or take other action including contacting said supervisor for additional direction when are not medically able to go to work;
- wherein upon said GS-HVS indicting that said individual user has good health, software displays a good health status or "Green Screen" on said individual user's said mobile device;
- providing software that recognizes any abnormal reporting from said individual user and provides alerts based on said protocol; and,
- providing software to a supervisor or medical advisor that facilitates advice to said individual user on any possible problems with said individual user based on said individual user's input to said GS-HVS.

18. The method of claim 17, further including the step of the software that allows said individual user to present said GS-HVS results as a screen view to a third party that said individual user desires to show the results to in order to confirm health status.

19. The method of claim 17, further including the step of the GS-HVS server embeds in the Green Screen a verification image code to confirm the authenticity of said Green Screen.

20. The method of claim 17, further including the step of the embedded image code contains a time stamp wherein the Green Screen validity expires after a specified amount of time.

* * * * *